(12) United States Patent
Mackool et al.

(10) Patent No.: US 8,579,929 B2
(45) Date of Patent: Nov. 12, 2013

(54) TORSIONAL ULTRASOUND HAND PIECE THAT ELIMINATES CHATTER

(75) Inventors: Richard J. Mackool, Astoria, NY (US); James Y. Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 283 days.

(21) Appl. No.: 12/875,461

(22) Filed: Sep. 3, 2010

(65) Prior Publication Data
US 2010/0324581 A1 Dec. 23, 2010

Related U.S. Application Data

(63) Continuation-in-part of application No. 11/608,283, filed on Dec. 8, 2006, now abandoned.

(51) Int. Cl.
*A61B 17/32* (2006.01)
(52) U.S. Cl.
USPC .............................................. 606/169; 604/22
(58) Field of Classification Search
USPC .................... 606/166, 167, 169, 170; 604/22
See application file for complete search history.

(56) References Cited

U.S. PATENT DOCUMENTS

| | | |
|---|---|---|
| 3,526,219 A | 9/1970 | Balamuth |
| 3,589,363 A | 6/1971 | Banko et al. |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |

(Continued)

FOREIGN PATENT DOCUMENTS

| | | |
|---|---|---|
| EP | 359217 | 3/1990 |
| WO | WO 8705793 | 10/1987 |

(Continued)

OTHER PUBLICATIONS

Shuyu, Lin. "Sandwiched Piezoelectric Ultrasonic Transducers of Logitudinal-Torsional Compound Vibrational Modes". IEEE Transactions of Ultrasonic, Ferroelectrics and Frequency Control, Nov. 1997, pp. 1189-1197.

(Continued)

*Primary Examiner* — Victor Nguyen
(74) *Attorney, Agent, or Firm* — Kenneth Bassinger (57) ABSTRACT

A torsional ultrasound surgical hand piece lessens or eliminates chatter from lens material by imparting a twisting, rotary motion to a tip of a phacoemulsification needle at a resonant frequency in excess of 32 kHz. The hand piece has a horn that is designed to operate at an elevated frequency while maintaining size constraints for hand-held ophthalmic instruments. Optionally, heat generation is reduced either through the use of a polyimide tubing situated between the needle and the infusion sleeve, through the use of thermal watch to prevent overheating at the incision, and/or through the use of a bypass hole in the needle that diverts flow under suction into the needle via the bypass hole instead of exiting through an irrigation opening in the infusion sleeve when a tip port is occluded by lens material.

18 Claims, 5 Drawing Sheets

(56) References Cited

U.S. PATENT DOCUMENTS

| | | |
|---|---|---|
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ames et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,171,387 A * | 12/1992 | Wuchinich .................... 156/73.3 |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,354,265 A | 10/1994 | Mackool |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,830,192 A | 11/1998 | Van Voorhis |
| 5,865,790 A | 2/1999 | Bair |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 * | 6/2002 | Boukhny ....................... 606/169 |
| 6,605,054 B2 | 8/2003 | Rockley |
| 6,629,948 B2 | 10/2003 | Rockley |
| 6,699,212 B1 | 3/2004 | Kadziauskas |
| 6,780,165 B2 | 8/2004 | Kadziauskas et al. |
| 7,374,552 B2 | 5/2008 | Wuchinich |
| 2001/0001123 A1 | 5/2001 | Madan et al. |
| 2001/0011176 A1 * | 8/2001 | Boukhny ....................... 606/169 |
| 2003/0045887 A1 | 3/2003 | Sakurai et al. |
| 2004/0092800 A1 | 5/2004 | MacKool |
| 2004/0092922 A1 | 5/2004 | Kadziauskas et al. |
| 2005/0267504 A1 * | 12/2005 | Boukhny et al. .............. 606/171 |
| 2006/0041200 A1 | 2/2006 | Dotter et al. |

FOREIGN PATENT DOCUMENTS

| | | |
|---|---|---|
| WO | WO 92/07622 | 5/1992 |
| WO | WO 99/45868 | 9/1999 |
| WO | WO 01/41672 | 6/2001 |
| WO | WO 2004/080505 | 9/2004 |

OTHER PUBLICATIONS

Jiromaru Tsujiino, "Ultrasonic Motor Using a One-Dimensional Logitudinal-Torsional Vibration Converter with Diagonal Slits", Smart Mater. Struct. 7 (1998), pp. 345-351.

* cited by examiner

TORSIONAL ULTRASOUND HAND PIECE THAT ELIMINATES CHATTER

CROSS-REFERENCE TO COPENDING PATENT APPLICATIONS

This application is a continuation-in-part of U.S. patent application Ser. No. 11/608,283, filed Dec. 8, 2006. Copending patent applications, whose contents are incorporated herein by reference, include: Ser. No. 10/183,591 filed Jul. 18, 2005 entitled Ultrasound Hand piece; Ser. No. 10/207,642 filed Aug. 19, 2005 entitled Method of Operating an Ultrasound Hand piece; Ser. No. 10/916,675 entitled Ultrasonic Hand piece, Ser. No. 11/189,274 filed Jul. 26, 2005 entitled Method of Controlling a Surgical System Based on Irrigation Flow; Ser. No. 11/189,492 filed Jul. 26, 2005 entitled Method of Controlling a Surgical System Based on a Load on the Cutting Tip of a Hand piece; and Ser. No. 11/189,624 filed Jul. 26, 2005 entitled Method of Controlling a Surgical System Based on a Rate of Change of an Operating Parameter.

BACKGROUND OF THE INVENTION

The present invention relates generally to the field of ophthalmic surgery and, more particularly, to reducing chatter when carrying out torsional ultrasound while dissipating heat at an incision during phacoemulsification.

The human eye functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light that can be transmitted to the retina. This deficiency is medically known as a cataract. An accepted treatment for cataracts is to surgically remove the cataract and replace the lens with an artificial intraocular lens (IOL). In the United States, the majority of cataractous lenses are removed using a surgical technique called phacoemulsification. During this procedure, a thin needle with a distal cutting tip is inserted into the diseased lens and vibrated ultrasonically. The vibrating cutting tip liquefies or emulsifies the lens so that the lens may be aspirated from the eye. The diseased lens, once removed, is replaced by an artificial intraocular lens (IOL).

A typical ultrasonic surgical device suitable for an ophthalmic procedure includes an ultrasonically driven hand piece, an attached cutting tip, an irrigating sleeve and an electronic control console. The hand piece assembly is attached to the control console by an electric cable or connector and flexible tubings. A surgeon controls the amount of ultrasound power that is delivered to the cutting tip of the hand piece and applied to tissue at any given time by pressing a foot pedal to request power up to the maximum amount of power set on the console. Flexible tubings supply irrigation fluid to and draw aspiration fluid from the eye through the hand piece assembly.

The operative part of the hand piece is a centrally located, hollow resonating bar or horn that is attached to a set of piezoelectric crystals. The crystals are controlled by the console and supply ultrasonic vibrations that drive both the horn and the attached cutting tip during phacoemulsification. The crystal/horn assembly is suspended within the hollow body or shell of the hand piece by flexible mountings. The hand piece body terminates in a reduced diameter portion or nose cone at the body's distal end. The nose cone is externally threaded to accept the irrigation sleeve. Likewise, the horn bore is internally threaded at its distal end to receive the external threads of the cutting tip. The irrigation sleeve also has an internally threaded bore that is screwed onto the external threads of the nose cone. The cutting tip is adjusted so that the tip projects only a predetermined amount past the open end of the irrigating sleeve.

In use, the ends of the cutting tip and the irrigating sleeve are inserted into a small incision of predetermined width in the cornea or sclera. One known cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the hand piece to the console. Other suitable cutting tips include piezoelectric elements that produce both longitudinal and torsional oscillations. One example of such a cutting tip is described in U.S. Pat. No. 6,402,769 (Boukhny), the contents of which are incorporated herein by reference.

A reduced pressure or vacuum source in the console draws or aspirates the emulsified tissue from the eye through the open end of the cutting tip, the cutting tip and horn bores and the aspiration line, and into a collection device. The aspiration of emulsified tissue is aided by a saline solution or other fluid that is injected into the surgical site through the small annular gap between the inside surface of the irrigating sleeve and the cutting tip.

One known surgical technique is to make the incision into the anterior chamber of the eye as small as possible in order to reduce the risk of induced post operative corneal curvature changes (astigmatism). These small incisions result in very tight wounds that squeeze the irrigating sleeve tightly against the vibrating tip. Friction between the irrigating sleeve and the vibrating tip generates heat. The risk of the tip overheating and burning tissue is reduced by the cooling effect of the aspirated fluid flowing inside the tip.

When the tip becomes occluded or clogged with emulsified tissue, the aspiration flow can be reduced or eliminated, which allows the tip to heat up. This practice also reduces cooling and results in a temperature increase, which may burn the tissue at the incision if left unchecked. In addition, during occlusion, a larger vacuum can build up in the aspiration tubing so that when the occlusion eventually breaks, a larger amount of fluid can be quickly suctioned from the eye, possibly resulting in the globe collapsing or other damage to the eye. Thus, it is important to dissipate the heat buildup at the incision to avoid tissue damage, and to prevent undesirable fluid surges from the eye during occlusion breaks.

Various heat generation reduction techniques are known. One way to reduce the amount of generated heat is to lessen the friction coefficient of the material that the vibrating phacoemulsification needle contacts. For instance, instead of allowing the needle to touch the rather sticky infusion sleeve made of liquid injection molded silicone, an intervening tubing made from a lower friction material such as polyimide may be employed to significantly reduce the amount of heat generated by friction. Another way is to divert irrigation flow though a bypass opening in the phacoemulsification needle in the event that the tip port of the needle becomes occluded by lens fragments. That way, irrigation flow continues to cool the needle despite the occlusion.

When the main tip port is not occluded, there will be virtually no difference in the through flow due to the presence of the bypass port, but typically clinically significant heating will occur when the main port is occluded by the lens fragments or viscoelastic material. In these cases, the presence of the bypass port can make a very significant difference by increasing flow from virtually zero to as much as 10 or perhaps more cc/min. That will result in an increase in cooling by a factor of 2-3, or perhaps even more, depending on many other factors, like the size of the sleeve used. The bypass port provides for accessory aspiration far away from the primary aspirating tip port at the distal end of the phacoemulsification needle. The bypass port is used to stabilize the anterior chamber during phacoemulsification when the primary aspirating tip is occluded. Reduction in heat generation may also be realized by lowering the vibration amplitude and/or reducing the operating duty cycle of the phacoemulsification tip.

The ultrasonically driven hand piece preferably provides torsional movement of the phacoemulsification tip. Torsional movement involves a twisting and preferably rotating movement of the tip about the longitudinal axis of the tip. Such torsional movement may be accomplished by the ultrasonic hand piece having a programmable ultrasound driver capable of producing both a torsional frequency drive signal and a longitudinal frequency drive signal. Such hand pieces are well-known to those in the art, with one example being described in U.S. Pat. No. 6,028,387 at column 2, line 6-67, column 3, lines 1-67 and FIGS. 2-3, such disclosure being incorporated herein by reference.

A conventional control system suitable for driving a torsional ultrasound hand piece may contain a drive circuit and preferably is similar to that described in U.S. Pat. No. 5,431,664, the entire contents of which being incorporated herein by reference, in that a drive circuit tracks the admittance of the hand piece and controls the frequency of hand piece to maintain a constant admittance.

The drive circuit monitors both the torsional mode and the longitudinal mode and controls these modes in the hand piece using two different drive frequencies. The torsional drive signal is approximately 32 kHz and the longitudinal drive signal is 44 kHz, but these frequencies will change depending upon the piezoelectric elements used and the size and shape of a horn. Although both the longitudinal or the torsional drive signal may be supplied in a continuous manner, preferably the longitudinal drive signal and the torsional drive signal are alternated. Such alternation enables the drive signal to be provided in a desired pulse at one frequency and then switched to the other frequency for a similar pulse, with no overlap between the two frequencies and no gap or pause in the drive signal. Alternatively, the drive signal can be operated in a similar manner as described, but short pauses or gaps in the drive signal can be introduced. In addition, the amplitude of the drive signal can be modulated and set independently for each frequency.

In the situation where chatter (visible vibration of lens fragments at the cutting tips) is present, high frequency movement of the vibrating lens or lens fragments is visibly apparent when viewed under the surgical microscope. When the lens or lens fragment vibrates less, the chatter is reduced. A softer lens will tend to chatter less, while a harder lens will tend to chatter more. Similarly, smaller fragments will tend to chatter more.

The extent that a lens is dense may be clinically estimated on a scale of 1-4 with 1 being non-compact or soft and 3-4 being dense or hard, but definitions may vary with the observer. For instance, what surgeons consider to be a hard lens in a developed part of the world will be softer than what surgeons consider to be a hard lens in the developing countries.

In the case of traditional ultrasound (longitudinal movement) along the tip axis, the lens fragments tend to be moved toward and away from the tip to give rise to chatter. In the case of torsional ultrasound (twisting movement) about the tip axis, the lens fragments move perpendicular to the tip axis and the chatter, if any, is much less than that present with traditional ultrasound for the same vibrational speed of oscillation. Nevertheless, on occasion when carrying out torsional ultrasound, chatter can still be observed when the tip is applied to very dense lenses while using a resonant frequency of 32 kHz. In addition, it is well known that lower resonant frequencies produce greater chatter.

It would be desirable to reduce or eliminate such chatter when employing torsional ultrasound on very dense or hard lenses.

SUMMARY OF THE PREFERRED EMBODIMENTS

It would be desirable to use torsional ultrasound at elevated resonant frequencies to reduce repulsion, while providing thermal mitigation at an incision. Such thermal mitigation may be realized with a heat generation reduction structure such as a bypass port or bypass hole in the phacoemulsification needle tip, low friction polyimide tubing around the tip, and/or flow and power dependent power modulation.

Current implementation of torsional ultrasound has torsional resonant frequency equal to about 32 kHz. This is somewhat lower than the typical 38 to 44 kHz used for longitudinal ultrasound. There is a slight amount of chatter associated occasionally with the torsional ultrasound especially when used on very dense lenses.

An increase in the frequency of torsional ultrasound results in a lower stroke for the same amount of energy transmitted to the lens. While this lower stroke is likely to invoke less movement of the lens, which will be perceived as less chatter and improved cutting performance, an increase in the torsional resonant frequency may result in an increase in the amount of heat dissipated at the incision to result in tissue damage. Such an increase in the heat dissipation at the incision can be mitigated in several ways.

It would be desirable to reduce the amount of heat generated at the incision by employing heat generation reduction structures such as those known conventionally. By interposing a polyimide tubing between the rather sticky or tacky infusion sleeve (made of liquid injection molded silicone) and the phacoemulsification needle, the phacoemulsification needle rubs against a surface with a lower coefficient of friction to lessen heat buildup that would otherwise arise. Further, making provision for the bypass port or bypass hole in the phacoemulsification needle enables irrigation flow through the phacoemulsification needle via the bypass port or bypass hole even through the main tip port is partially or fully occluded by lens fragments or viscoelastic material.

In addition, lowering vibration amplitude and/or reducing the operating duty cycle of the phacoemulsification tip helps to reduce heat generation.

A reduction in heat will be approximately proportional to reduction in the power of ultrasound, the reduction in ultrasound duty cycle, and the increase in the amount of flow through the system. The amount of fluid going through the bypass hole will vary significantly.

One aspect of the invention resides in a torsional ultrasound surgical instrument that includes a surgical hand piece suited for phacoemulsification. The hand piece includes a phacoemulsification needle that is hollow to define an aspiration passage and that distally terminates into a tip with a tip port, the tip being bent or angled. The hand piece also includes an infusion sleeve that is flexible and arranged radially outside of the phacoemulsification needle so as to define therebetween an irrigation passage to channel irrigation flow. The infusion sleeve defines an irrigation opening arranged for the irrigation flow to exit the irrigation passage. A driver is configured and arranged to impart a twisting, rotative movement to the tip at an elevated resonant frequency in excess of 32 kHz and sufficient to eliminate chatter otherwise present at lower resonant frequencies. A heat generation reduction structure is provided that is configured and arranged to reduce heat generation that would otherwise occur as a consequence of the driver imparting the twisting, rotative movement to the tip at the elevated resonant frequency instead of at the lower resonant frequencies.

Another aspect resides in the heat generation reduction structure being a bypass hole in the phacoemulsification needle. The bypass hole is configured and arranged to divert the irrigation flow from the irrigation passage to enter the aspiration passage under suction via the bypass hole when the port is occluded and thereby reduce the temperature of the needle.

Still another aspect resides in the heat generation reduction structure being a tubing that is elongated and situated between the infusion sleeve and the phacoemulsification needle. The tubing has a texture that is less tacky than that of the infusion sleeve and provides less friction resistance to rubbing action than the infusion sleeve. The tubing may be made of polyimide material.

Yet another aspect resides in the heat generation reduction structure including a controller of the drive that directs the drive to alter an amount, duration and type of ultrasound power applied to the tip of the phacoemulsification needle based on an analysis that tracks a history of the ultrasound power over time and its effect on changing temperature.

A further aspect resides in the heat generation reduction structure including a controller of the drive that directs the drive to introduce pauses in the twisting, rotative movement and/or to vary an amplitude of the ultrasound power being applied.

BRIEF DESCRIPTION OF THE DRAWING

For a better understanding of the present invention, reference is made to the following description and accompanying drawings, while the scope of the invention is set forth in the claims.

DESCRIPTION OF THE PREFERRED EMBODIMENT

The present invention is directed to a torsional ultrasound surgical instrument that has a phacoemulsification capability, a torsional ultrasound capability, a heat generation reduction capability and a chatter elimination capability.

Torsional phacoemulsification has two main advantages when compared with traditional ultrasound: efficiency in nucleus removal and safety in terms of reduced risk of thermal injury. Nucleus removal refers to the removal of lens fragments. Unlike traditional ultrasound, there is no forward and backward movement of the tip with torsional ultrasound.

In the torsional mode, the hand piece oscillates from side to side at about 32,000 times per second. This side-to-side motion shears off nucleus pieces without repelling them, thus lessening if not eliminating chatter. Using the same flow and vacuum settings that might normally be set for traditional ultrasound, the cataract surgeon will notice that the nucleus is removed more quickly with torsional ultrasound.

The nucleus appears to evaporate. It just disappears into the tip quickly because it doesn't just sit on the tip and microscopically chatter during removal. This difference between traditional and torsional ultrasound is particularly noticeable with more dense lenses.

In the case of extremely dense lenses (4+), there may be the need to use a combination of torsional and traditional longitudinal ultrasound to avoid obstruction of the hand piece tip. The obstruction may be caused by a large sheared-off piece obstructing the tip. To avoid that problem, the torsional hand piece can be programmed to deliver a percentage of the ultrasonic energy by the traditional to and fro method.

Such a method involves simply pushing a button to change hand piece function from, for example, 100% torsional to a combination of 80% torsional oscillation and 20% traditional ultrasound. In such a case, the duty cycle would be 80 msec on for torsional and 20 msec on for traditional.

The torsional hand piece, weighing only 1.5 ounces, has a tip that is angled and tapered, so that the distal end is wider than the shaft. Different-sized infusion sleeves can be used with the hand piece, thus enabling a small incision of 2 to 2.2 mm or less.

For very small incisions, a torsional hand piece with the ULTRASLEEVE™ (Alcon) may be used at a maximum aspiration flow of 40 ml/min, a maximum vacuum of 400 mm Hg, and an infusion bottle height of 135 cm. To increase the parameters to an aspiration flow rate of 50 ml/min and a maximum vacuum setting of 550 mm Hg, a high-infusion sleeve may be used.

Torsional ultrasound provides a reduced thermal effect compared with traditional ultrasound. The reason is that the velocity of the angled tip of the torsional hand piece is about three times greater than the velocity of its shaft. Thus, the amount of energy being released at the tip is much greater than the amount of heat being created by the shaft within the incision. In traditional ultrasound, the velocity at the tip and the velocity at the shaft in the incision are equal, which creates a greater chance for thermal injury.

Figure 1:
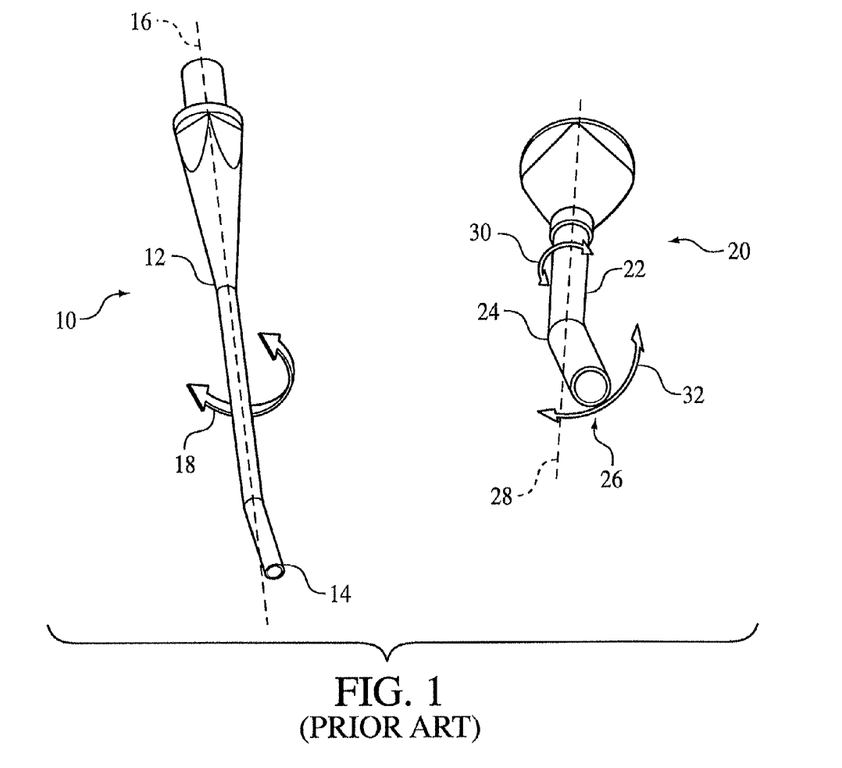
FIG. 1 is a comparative view of conventional longitudinal and torsional hand piece movements for phacoemulsification.

FIG. 1 illustrates a comparison between longitudinal phacoemulsification and torsional phacoemulsification. In the case of the former, a longitudinal surgical phacoemulsification hand piece tip 10 is used that has an elongated shaft 12 and a bent or angled tip 14 at its distal end that tapers. The tip 10 rotates about an axis of rotation 16. By oscillating the shaft 12 through an arc 18, the cutting edge of the bent or angled tip 14 likewise traverses an arc of about the same dimension.

In the case of torsional phacoemulsification, the torsional phacoemulsification surgical hand piece tip 20 likewise includes a shaft 22 and bent or angled tip 24 with a cutting edge 26, but the twisting motion imparted on the hand piece tip 20 limits movement of the shaft 22 of the torsional hand piece as compared to the oscillatory rotary movement of the shaft 12 for longitudinal phacoemulsification. The amount of motion at the incision is very small with torsional phacoemulsification as compared to traditional or longitudinal phacoemulsification.

When the torsional phacoemulsification surgical hand piece oscillates about a longitudinal axis 28, only a small arc 30 is created at the incision compared with the arc 32 created at the angled tip ù a 3:1 difference for the cutting edge 26 to traverse. The bent or angled tip 24 in effect undergoes a whipping motion that increases cutting efficiency over that of longitudinal phacoemulsification since it may cut continuously, as opposed to cutting just on the forward stroke while not cutting on the backward stroke.

The torsional phacoemulsification surgical hand piece produces much less energy or friction at the incision. Thermal imaging studies performed in cadaver eyes have showed the temperature differences of traditional ultrasound versus torsional. At 100% power and total occlusion (no flow) for 25 seconds, traditional ultrasound produced 70° C. at the incision, whereas the torsional ultrasound incision only reached 40° C.

However, thermal injury is still possible. The risk of burning the incision also is proportional to how hard the surgeon presses the vibrating tip against the surrounding tissue. If the surgeon forcibly decenters a tip within an incision and pushes it against the surrounding tissue, the risk of thermal injury will greatly increase regardless of whether the surgeon is using torsional ultrasound or traditional ultrasound. Experienced surgeons are aware of this and attempt to avoid tip decentration.

The efficiency of torsional ultrasound over traditional longitudinal ultrasound has been observed in practice and is attributed to the tip's oscillation speed of 32 kHz. Every complete stroke of the tip, one side to another and back, is like two strokes, i.e., it functions as if it were a 64 kHz hand piece. With traditional ultrasound, the forward and backward motion of the tip is at a speed of 38 kHz, but only the forward movement of the tip impacts the nucleus.

With a higher power setting for traditional phacoemulsification, the surgeon will experience increased chatter, and the increased energy delivered into the eye will not be maximally directed at and absorbed by the nucleus. The increased energy released within the eye can adversely affect structures such as the iris or the corneal endothelium.

With torsional phacoemulsification, watertight incisions can be created because there is no need for leakage at the incision to cool the instrument. Removal of the nucleus can be completed in half the time of traditional ultrasound using about half of the usual amount of total flow through the eye, and the surgeon can maintain a stable anterior chamber throughout the surgery.

Figure 2:
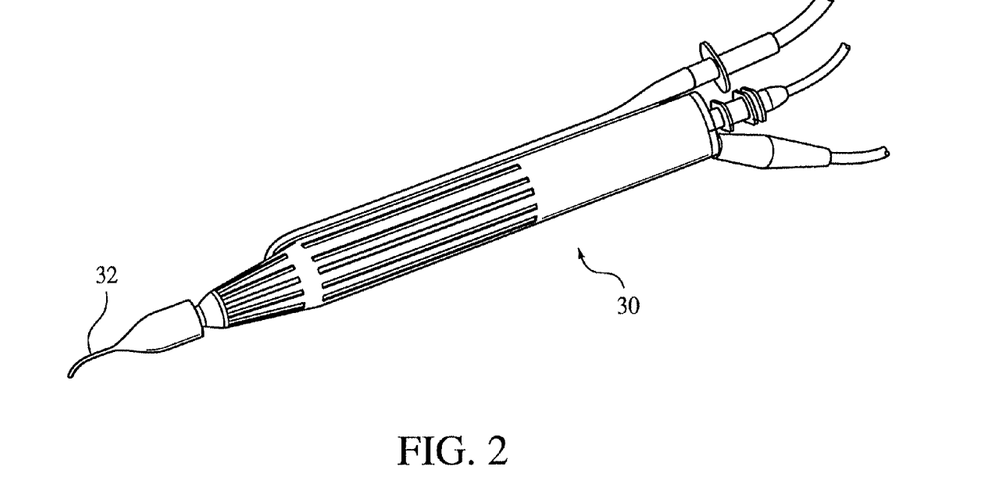
FIG. 2 is a side view of a torsional hand piece in accordance with the invention.

FIG. 2 shows a torsional hand piece 30 in accordance with the invention that has a bent or angled tip 32. The outward appearance may look the same as the ultrasonic and piece commercialized with the INFINITI" Vision System of Alcon Research, Inc. under the trade name OZIL™, but there are differences that enable the torsional ultrasound to be performed at elevated resonant frequencies. These differences are described more fully with reference to FIGS. 3-5.

Figure 3:
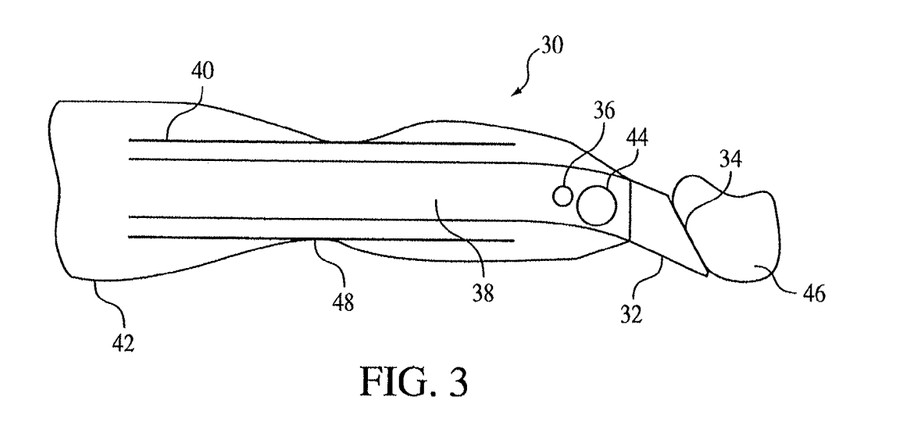
FIG. 3 is a schematic representation of an occluded phacoemulsification tip with bypass hole, polyimide tubing and infusion sleeve.

FIG. 3 shows a diagram of a torsional ultrasound hand piece 30, which is part of a torsional ultrasound surgical instrument in accordance with the invention. The torsional ultrasound hand piece 30 includes the bent or angled tip 32 that tapers and whose distal edge defines a tip port 34. A bypass port or bypass hole 36 is provided in the phacoemulsification needle 38 at a distance spaced away from the tip port 34. A heat generation reduction tubing 40, which constitutes a heat generation reduction structure, is arranged radially outside of the phacoemulsification needle 38. A flexible infusion sleeve 42 is arranged radially outside of the heat generation reduction tubing 40. The infusion sleeve includes one or more irrigation openings 44 to allow irrigation flow to exit the gap that is defined between the phacoemulsification needle 38 and the infusion sleeve 42.

The infusion sleeve 42 is conventional and has a tacky texture that may be considered somewhat sticky in that there is greater heat buildup caused by friction from the phacoemulsification needle rubbing against it than is the case when the phacoemulsification needle rubs against the heat generation reduction tubing 40.

The infusion sleeve 42 is made from liquid injection molded silicone, which has desired biocompatibility, compliance, and structural properties. However, a disadvantage of this material is that it has an extremely high friction coefficient in that this material has a tacky texture.

Figure 4:
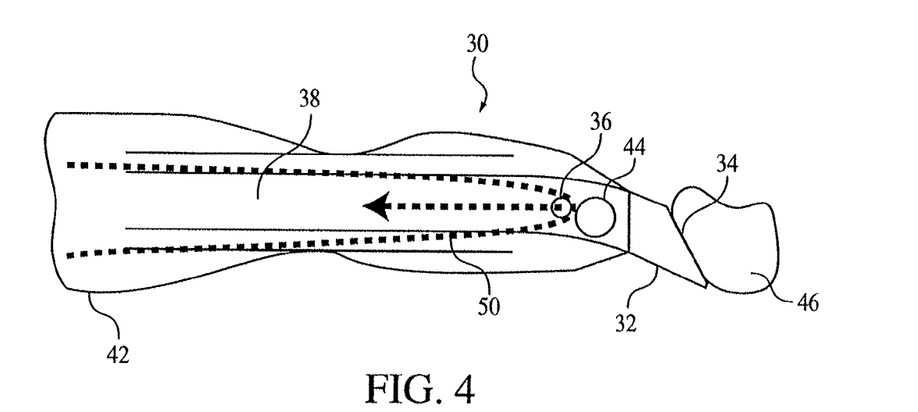
FIG. 4 is a schematic flow diagram of an occluded phacoemulsification tip port that depicts a flow diversion path for irrigation flow through a bypass hole to enter a hollow interior of the phacoemulsification needle.
Figure 5:
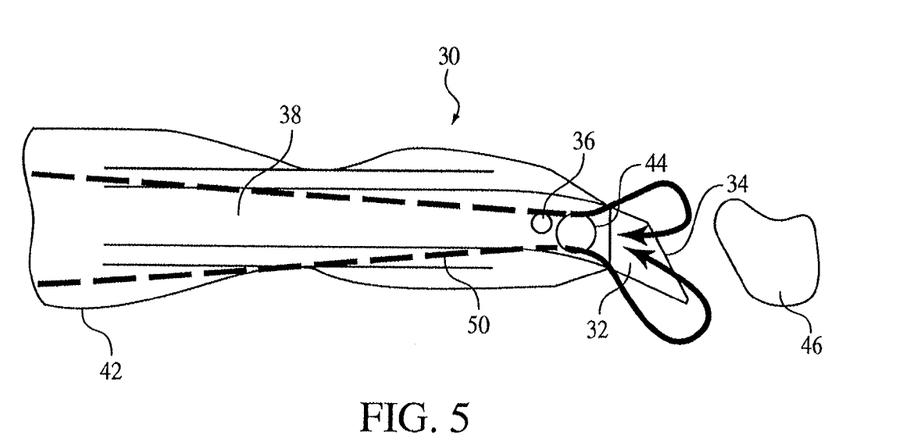
FIG. 5 is a schematic flow diagram of an unoccluded phacoemulsification tip port that depicts an irrigation flow path that exits through an irrigation opening to become sucked into a hollow interior of the phacoemulsification needle via the unoccluded phacoemulsification tip port

The heat generation reduction tubing 40 is conventional, preferably made of polyimide as known from U.S. Pat. No. 5,830,192 for rigid sleeve materials. The placement of a rigid sleeve of this type between the infusion sleeve 22 and the phacoemulsification needle 38 is generally known from U.S. Pat. No. 5,354,265 and U.S. Pat. No. 5,286,256, each of whose contents are incorporated herein by reference. The heat generation reduction tubing 40 may be held in place by a bend in the phacoemulsification needle as shown in FIGS. 3-5.

The phacoemulsification needle 38 is conventional, preferably made of a metal such as titanium or stainless steel alloy. Nucleus pieces 46, such as cataractous lens fragments, typically pass under suction through the hollow interior of the phacoemulsification needle 38 via the tip port 34. Preferably, the phacoemulsification needle 38 has its own heat generation reduction structure in the form of an bypass port or bypass hole 36, such as that exemplified in U.S. Pat. No. 6,605,504. Thus, in the event that the tip port 34 becomes partially or fully occluded by nucleus pieces 46, irrigation fluid is drawn through the bypass hole 36 under suction rather than exit through an irrigation opening 44 in the infusion sleeve 42.

The infusion sleeve 42 is compressed by the incision 48 tightly and pressed against the heat generation reduction tubing 40. This is the region where heat may buildup to cause tissue damage if left unchecked. However, by employing the heat generation reduction structures, such heat buildup is avoided.

Indeed, the amount of frictional heat generated at the incision is proportional to the frictional force of the frictional pair undergoing a rubbing action. Thus, by having the frictional pair consist of the phacoemulsification needle 38 and the heat generation reduction tubing 40, the amount of frictional heat generated at the incision is as much as two times less than would be the case if the frictional pair were the phacoemulsification needle 38 and the silicone infusion sleeve 42 for the same vibration velocity of the tip and the same normal force between the tip and the material the tip touches.

The effect of the bypass hole 36 on irrigation flow is illustrated in FIGS. 4 and 5. In the case of FIG. 4, the tip port 34 is occluded by nucleus pieces 46, such as cataractous lens fragments or viscoelastic material. As a consequence, the irrigation flow 50 enters the bypass hole 38 to be aspirated through the hollow of the phacoemulsification needle 38 instead of exiting through the irrigation opening 44 in the infusion sleeve 42. In the case of FIG. 5, the tip port 34 is not occluded by the nucleus pieces 46 so that the irrigation flow 50 exits through the irrigation opening 44 to enter the eye and be suctioned through the tip port 34 to pass through the hollow interior of the phacoemulsification needle 38.

If desired, a conventional thermal watch algorithm may be employed to regulate the amount of power delivered to the torsional ultrasound hand piece 10 to prevent overheating, such as that described in Ser. No. 11/189,624, whose contents regarding thermal watch are incorporated herein by reference. The thermal watch algorithm may involve direct measurement of the irrigation flow or calculating irrigation flow from bottle height and irrigation pressure sensor. By tracking the history of application of ultrasound power over time, one can calculate estimated temperature increase at the incision. The amount of heat dissipated at the incision can be decreased by altering amount, duration and type of ultrasound power applied.

For example, pauses can be introduced during phacoemulsification power application and/or the duration of ultrasound power pulses can be shortened. Further, the amplitude of ultrasound pulses can be decreased. In addition, torsional ultrasound at the same or lower power and/or duration can be applied instead of continuous application of longitudinal ultrasound. Indeed, torsional ultrasound requires the dissipation of approximately ⅓ the amount of heat for the same power as longitudinal ultrasound.

The amount of heat created is proportional to the amplitude of tip vibration and duty cycle. Thus, reducing either will reduce amount of heat generation. The amount by which heat needs to be reduced is determined by the temperature at the incision. While there isn't currently a practical way to measure this temperature, it is conventional to predict it assuming a certain amount of friction at the tip and measuring the amount of irrigation flow.

It is important to lower the amount of heat generation so as to not approach clinically damaging levels of temperature. Typically, these levels of temperature are between 45 and 50 degrees Centigrade, depending on the duration of the temperature exposure. The greater the temperature, the faster irreversible damage to ocular tissues will occur.

Figure 6:
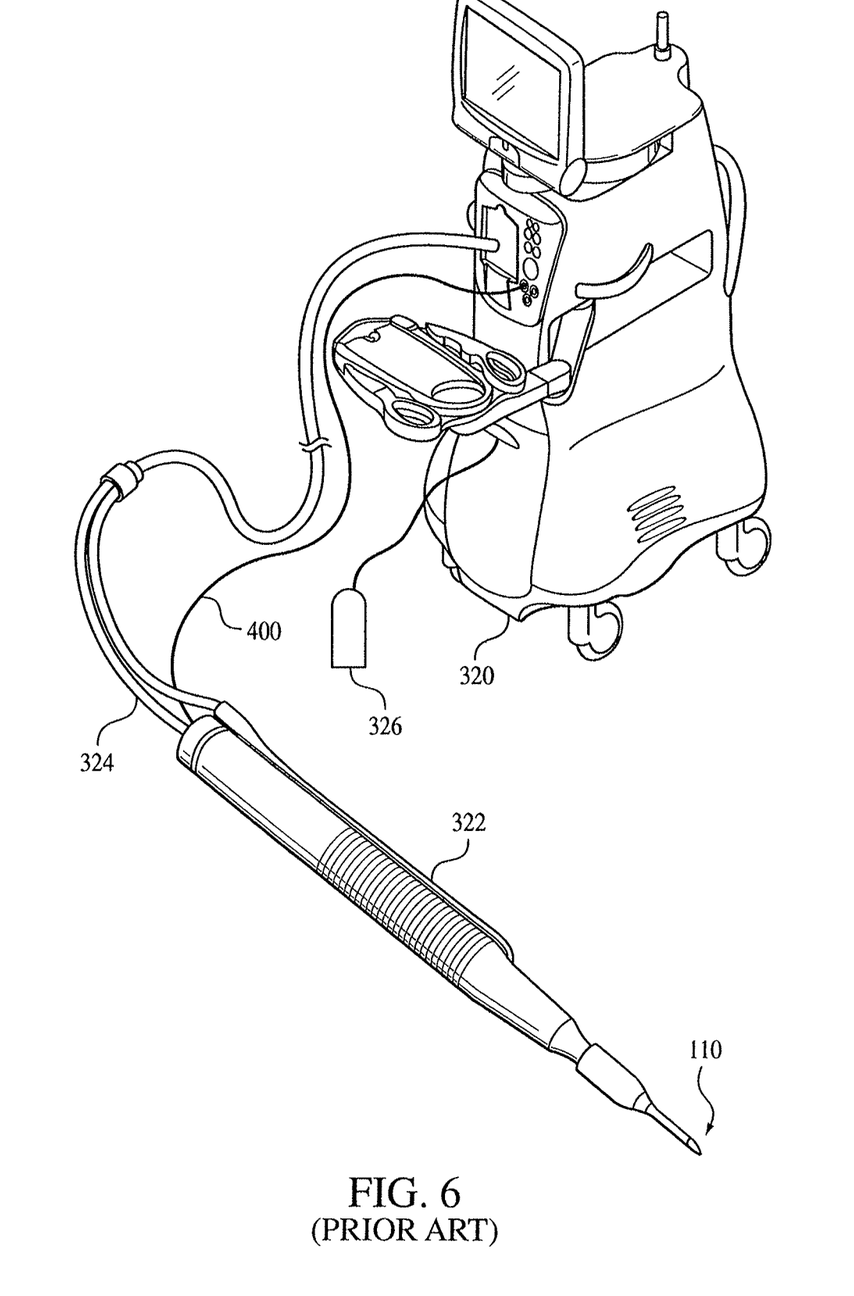
FIG. 6 is an isometric view of a conventional hand piece and control console that may be readily adapted for use with the present invention.

FIG. 6 is essentially the same as FIG. 1 of U.S. Ser. No. 11/232,295, which exemplifies the conventional surgical console 320 suitable for use with the present invention and is incorporated herein by reference. The console 322 is exemplified by the INFINITI® Vision Systems available from Alcon Laboratories, Inc. of Fort Worth, Tex. Console 320 is connected to hand piece 9 through irrigation line 322 and aspiration line 324. The flow through lines 322 and 324 is controlled by the user, for example, via foot switch 326. Power is supplied to the ultrasonic hand piece 9 through electrical cable 400. The phacoemulsification needle tip 110 is bent or angled.

The hand piece 9 may be replaced by the torsional hand piece 30. Indeed, the torsional hand piece 30 may be further modified to resemble the ultrasonic hand piece of U.S. Ser. No. 10/916,675 that has a horn made of titanium alloy. The horn has helical slits and piezoelectric elements are held by a compression nut against the horn. An aspiration shaft extends down the length of the hand piece through the horn, piezoelectric elements, nut and plug at a distal end of the hand piece. The resonant frequency will change depending upon the piezoelectric elements uses and the size and shape of the horn and slits.

The longer the horn, the lower the resonant frequency will be. A conventional finite element analysis may be performed to determine the exact shape of the horn that would be suitable for a particular resonant frequency. The piezoelectric elements, slits and length of the horn may be varied to enable operation at a different resonant frequency such as 40 kHz. The heat dissipation techniques of FIGS. 3-5 are readily driven by the surgical system of FIG. 6.

Figure 7:
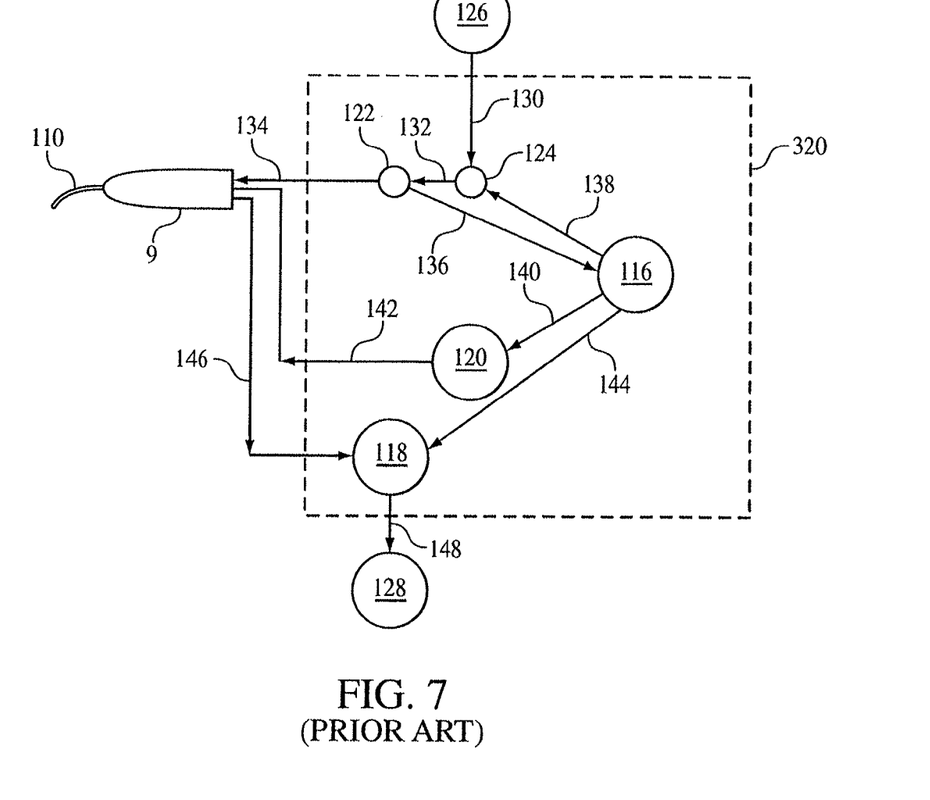
FIG. 7 is a block diagram showing components of a conventional surgical system employed in FIG. 6 that may be adapted for use with the present invention.

FIG. 7 is essentially the same as FIG. 2 of U.S. Ser. No. 11/189,374, which shows a control system within the console 322 of FIG. 6 used to operate the conventional ultrasonic hand piece 9. The console 322 has a control module of CPU 116, an aspiration, vacuum or peristaltic pump 118, a hand piece power supply 120, an irrigation pressure sensor 122 and a valve 124.

The CPU 116 may be any suitable microprocessor, microcontroller, computer or digital logic controller. The pump 118 may be a peristaltic, diaphragmatic, a venturi or other suitable pump. The power supply 120 may be any suitable ultrasound driver, such as incorporated in the INFINITI" Vision System available from Alcon Laboratories, Inc. The valve 124 may be any suitable valve such as a solenoid-activated pinch valve. An infusion of an irrigation fluid, such as saline, may be provided by a saline source 126, which may be any commercially available irrigation solution provided in bottles or bags.

In use, the irrigation pressure sensor 122 is connected to the hand piece 9 and the infusion fluid source 126 through irrigation lines 130, 132 and 134. The irrigation pressure sensor 122 measures the pressure of irrigation fluid from the source 126 to the hand piece 112 and supplies this information to the CPU 116 through the cable 136. The irrigation fluid pressure data may be used by the CPU 116 to control the operating parameters of the console 320 using software commands. For example, the CPU 116 may, through a cable 140, vary the output of the power supply 120 being sent to the hand piece 9 and the tip 110 though a power cable 142.

The CPU 116 may also use data supplied by the irrigation pressure sensor 122 to vary the operation of the pump 118 through a cable 144. The pump 118 aspirates fluid from the hand piece 9 through a line 146 and into a collection container 128 through line 148. The CPU 116 may also use data supplied by the irrigation pressure sensor 122 and the applied output of power supply 120 to provide audible tones to the user. Additional details concerning such surgical systems can be found in U.S. Pat. No. 6,179,808 (Boukhny, et al.) and U.S. Pat. No. 6,261,283 (Morgan, et al.), the entire contents of which are incorporated herein by reference.

In one embodiment, the control console 320 (FIG. 6) can control the amount of power that is delivered to the hand piece 9 based on the stage of an occlusion event. More particularly, power adjustments are made based on changes of an aspiration vacuum level, an irrigation pressure level, or both aspiration vacuum and irrigation pressure levels. The change can be, for example, a rate of change of the increase or decrease of aspiration vacuum and/or irrigation pressure.

Initially, a pattern of a surgical operating parameter during an occlusion or other surgical event is detected over a period of time. The operating parameter can be a vacuum pressure and/or an irrigation pressure. Both pressures can also be detected; however, reference is primarily made to a single operating parameter for purposes of explanation, not limitation. The values and/or the rate of change of the operating parameter can be determined or calculated. Based on this calculation, a stage of an occlusion is determined. The amount of power that is delivered to a cutting tip of the hand piece 9 can be adjusted, as necessary, based on the stage of occlusion.

More specifically, it has been determined that aspiration vacuum and irrigation pressure levels follow a detectable pattern before, during and after an occlusion. This pattern can be used to identify a stage of an occlusion and adjust the power delivered to the hand piece 9 accordingly.

The cutting portion of the phacoemulsification tip is preferably made from stainless steel or titanium, but other materials may also be used and preferably it is electropolished to remove any burrs.

When torsional motion is applied via ultrasound power to the conventional surgical systems that impart a twisting motion at 32 kHz resonant frequency, occasionally some chatter may be observed for dense lenses. By modifying such conventional systems in accordance with the invention so as to elevate the resonant frequency to as much as 40 kHz or more, such chatter is eliminated. The modifications involve dimensional changes.

The resonant frequency need not be exactly 40 kHz. It could be somewhat higher or lower to effectuate the reduction or elimination of chatter that is occasionally observed when torsional ultrasound is used on dense lenses (when the resonant frequency is 32 KHz.). However, the heat dissipation techniques of FIGS. 3-5 preferably should be implemented.

The amount of energy dissipated at the incision, the only clinically relevant heat, is proportional to the tip velocity at the incision. The tip velocity is proportional to the frequency at which the tip oscillates (which is very close to the resonant frequency) times the stroke length of the tip at the incision. The stroke of the tip at the incision is proportional to the stroke of the tip at the cutting edge. Therefore, the amount of clinically relevant heat is proportional to the product of resonant frequency and stroke length at the cutting edge.

As a result of limiting the energy transferred to the hand piece or limiting the amount of heat dissipated at the incision, a higher resonant frequency will result in lower stroke at the cutting edge. The less the stroke is at the cutting edge, the less will be the impulse transferred to the lens and the less will be apparent vibration of the lens, also referred to as lens chatter.

The amount of energy transferred into the eye is proportional to the stroke length and frequency. Therefore, if one were to maintain constant energy, an increase in frequency will require a proportional decrease in stroke length. The shorter the stroke, the less chatter there is going to be as the lens is not moved as far by the vibrating needle.

Figure 8:
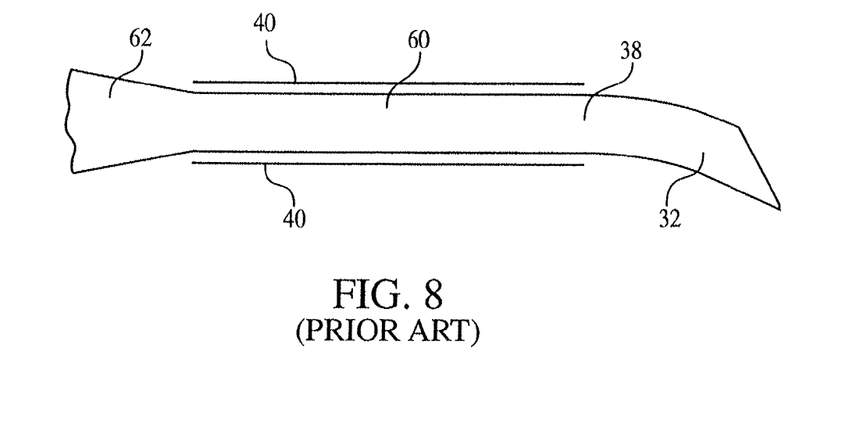
FIG. 8 is a schematic representation of a conventional phacoemulsification needle tip and polyimide tubing.

FIG. 8 shows a conventional phacoemulsification needle 38 with bent or angled tip 32. The needle 38 includes a straight portion 60 of generally uniform cross section along its length and a hub 62 that tapers to the proximal side of the straight portion 60. The bent or angled tip 32 extends outwardly from the distal side of the straight portion 60. The heat generation reduction tubing 40 encircles the straight portion 60.

The heat generation reduction tubing 40 as well as the phacoemulsification needle 38 is circular. The inner diameter of the heat generation reduction tubing is only slightly larger than the outer diameter of the phacoemulsification needle 38 on which it is mounted. Polyimide, which is a material for the tubing 40, does have some flexibility since the tubing 40 is thin—usually between 0.002" and 0.003". It is possible to deform the tubing 40 and push it over the bend of the tip 32. It will remain there as long as there isn't a deliberate effort to remove it from the tip 32. This level of retention is sufficient for typical cataract surgery. Such an arrangement and configuration of components in FIG. 8 may be exchanged for the arrangement and configuration of like components of FIGS. 3-5.

Figure 9A:
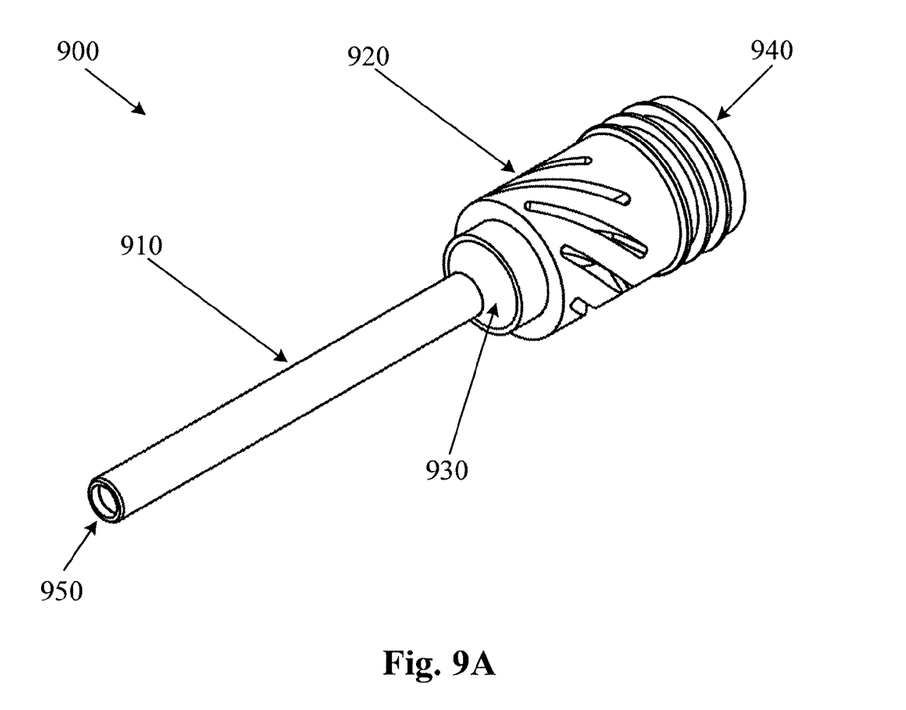
FIGS. 9A and 9B are perspective and side views, respectively, of an ultrasonic horn according to the principles of the present invention.
Figure 9B:
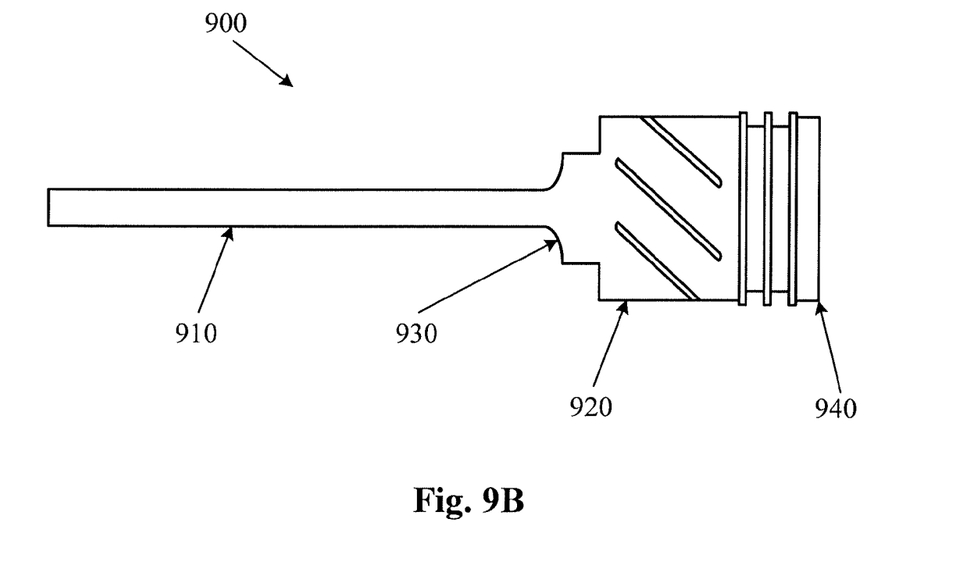

FIGS. 9A and 9B are perspective and side views, respectively, of a horn consistent with the principles of the present invention. Horn 900 is contained in hand piece 30 of FIG. 2. Distal end 950 of horn 900 is coupled to phacoemulsification needle 38, typically via a threaded connection. Coupling end 940 of horn 900 is located in the shell of the hand piece 30 shown in FIG. 2. Coupling end 940 is coupled to a transducer, typically a set of piezoelectric crystals. The distal section 910 is coupled to the resonant section 920 via collar 930—all of which are typically made of a single piece of material such as a titanium alloy. The spiral slits in resonant section 920 convert motion imparted by the transducer into either longitudinal or torsional motion at distal end 950 as described below.

Horn 900 is designed to resonate at two different frequencies—a longitudinal resonant frequency and a torsional resonant frequency. When horn 900 resonates at the longitudinal resonant frequency, phacoemulsification needle 38 vibrates longitudinally (or back and forth). When horn 900 resonates at the torsional resonant frequency, phacoemulsification needle 38 vibrates torsionally (in a twisting manner or side to side). As noted, a transducer is coupled to coupling end 940 of horn 900. The transducer vibrates longitudinally (back and forth). When the transducer vibrates at the longitudinal resonant frequency, the horn 900 resonates longitudinally—it compresses and expands along its axis at the longitudinal resonant frequency. When the transducer vibrates at the torsional resonant frequency, the horn 900 resonates torsionally—it twists along its axis at the torsional resonant frequency (i.e. the longitudinal motion of the transducer is converted to torsional motion at the distal end 950 by horn 900). This twisting motion imparts a side to side motion at the end of phacoemulsification needle 38.

The frequency at which the horn 900 resonates determines the stroke or movement of the phacoemulsification needle 38. Higher frequencies produce a higher needle stroke or faster needle movement. A higher needle stroke or faster needle movement results in an increased number of needle contacts with the cataractous lens. In other words, the higher the frequency, the more the needle 38 makes contact with, and consequently fragments, the cataractous lens. Therefore, all other things being equal, a higher frequency can result in a faster surgery time. It is also instructive to note that the amount of power supplied to the hand piece is directly proportional to the stroke length (or the distance the distal end of needle 38 travels). Higher power results in a longer stroke length (or longer travel of needle 38). When vibrating torsionally, a higher power results in a greater back and forth movement of the distal end of needle 38. Lower power results in less movement of the distal end of needle 38.

As noted above, when power is increased to the hand piece 30, the greater movement of the distal end of needle 38 can result in lens chatter. When resonating torsionally, lens fragments can chatter at the distal end of needle 38. Decreasing power can eliminate lens chatter which can result in more efficient cutting. However, decreasing power can also result in a longer surgery time as the distal end of needle 38 makes less powerful contact with the lens. If frequency is increased while power is decreased, more efficient cutting can result as the distal end of needle 38 makes more contact with the lens during a given period of time at a lower power that results in less chatter (and potentially less heat as well). In this manner, the total power to the hand piece can be reduced while the frequency is increased so as to produce the same amount of lens cutting with lower power. While the displacement of any individual needle stroke is decreased, the total number of needle strokes can be increased (by increasing the resonant frequency).

In order to operate at a higher resonant frequency, horn 900 is designed as shown in FIGS. 9A and 9B. In FIGS. 9A and 9B, the resonant section 920 of horn 900 is reduced in length while the distal section 910 of horn 900 is increased in length. In one embodiment of the present invention, the distal section 910 has a greater length than the resonant section 920. In another embodiment of the present invention, the distal section 910 occupies about 65% of the total length of horn 900, while the resonant section 920 occupies about 35% of the total length of horn 900. In these embodiments, the horn may be between 2.5 and 3.0 inches in length. This design allows for higher resonant frequencies (of greater than 40 kilohertz, and more preferably greater than 50 kilohertz) while keeping the overall length of the horn 900 suitable for use in a hand held ophthalmic instrument. The overall length of the horn being between 2.5 and 3.0 inches allows it to be incorporated into a hand piece 30 that is suitable for ophthalmic surgery. By decreasing the length of the resonant section 920 and increasing the length of the distal section 910, the horn 900 operates at a higher resonant frequency of greater than 40 kilohertz (and preferably greater than 50 kilohertz) while still being able to fit in hand piece 30.

This description is given for purposes of illustration and explanation. It will be apparent to those skilled in the relevant art that changes and modifications may be made to the invention described above without departing from its scope.

What is claimed is:

1. An ophthalmic ultrasound surgical instrument, comprising:
    a surgical hand piece suited for phacoemulsification that includes a phacoemulsification needle that is hollow to define an aspiration passage and that distally terminates at a tip with a tip port, the needle being bent or angled;
    an infusion sleeve arranged radially outside of the needle so as to define therebetween an irrigation passage to channel irrigation flow, the infusion sleeve defining an irrigation opening arranged for the irrigation flow to exit the irrigation passage;
    a heat generation reduction structure configured to reduce heat present at the needle, wherein the heat generation reduction structure includes a bypass hole in the phacoemulsification needle, the bypass hole being configured to divert the irrigation flow from the irrigation passage to enter the aspiration passage under suction via the bypass hole while the port is obstructed and thereby prevent the irrigation flow from otherwise exiting through the irrigation opening;
    a horn with a distal section and a resonant section, the distal section being longer than the resonant section, the distal section and the resonant section each having a generally cylindrical shape, the distal section having a cross sectional area that is less than the cross sectional area of the resonant section, the horn coupled to the needle; and
    a driver configured to impart a twisting, rotative movement to the tip at an elevated resonant frequency sufficient to eliminate chatter otherwise present at lower resonant frequencies.

2. The instrument of claim 1 further comprising a controller of the driver that directs the driver to alter an amount, duration or type of ultrasound power imparted to the tip of the phacoemulsification needle based on an analysis that tracks a history of the ultrasound power over time and its effect on changing temperature.

3. The instrument of claim 1 further comprising a controller of the driver that directs the driver to introduce pauses in the twisting, rotative movement.

4. The instrument of claim 1 further comprising a controller of the driver that directs the driver to vary an amplitude of the ultrasound power being applied.

5. The instrument of claim 1, wherein the driver is configured to impart the twisting, rotative movement to the tip at a resonant frequency of at least 40 kHz.

6. The instrument of claim 1, further comprising a controller of the driver that directs the driver to vary a duty cycle of the ultrasound power being applied.

7. The instrument of claim 1, further comprising a controller that tracks a history of ultrasound power over time.

8. The instrument of claim 1, further comprising a controller that tracks a temperature.

9. An ophthalmic ultrasound surgical instrument, comprising:
    a surgical hand piece suited for phacoemulsification that includes a phacoemulsification needle that is hollow to define an aspiration passage and that distally terminates at a tip with a tip port, the needle being bent or angled;
    an infusion sleeve arranged radially outside of the needle so as to define therebetween an irrigation passage to channel irrigation flow, the infusion sleeve defining an irrigation opening arranged for the irrigation flow to exit the irrigation passage;
    a heat generation reduction structure configured and arranged to reduce heat present at the needle;
    a horn with a distal section and a resonant section, the distal section being longer than the resonant section, the horn coupled to the needle; and
    a driver configured and arranged to impart a twisting, rotative movement to the tip at an elevated resonant frequency sufficient to eliminate chatter otherwise present at lower resonant frequencies;
    wherein the heat generation reduction structure includes a bypass hole in the phacoemulsification needle, the bypass hole being configured and arranged to divert the irrigation flow from the irrigation passage to enter the aspiration passage under suction via the bypass hole while the port is obstructed and thereby prevent the irrigation flow from otherwise exiting through the irrigation opening.

10. An ophthalmic ultrasound surgical instrument, comprising:
    a surgical hand piece suited for phacoemulsification that includes a phacoemulsification needle that is hollow to define an aspiration passage and that distally terminates at a tip with a tip port, the needle being bent or angled;
    an infusion sleeve arranged radially outside of the needle so as to define therebetween an irrigation passage to channel irrigation flow, the infusion sleeve defining an irrigation opening arranged for the irrigation flow to exit the irrigation passage;
    a heat generation reduction structure configured and arranged to reduce heat present at the needle;
    a horn with a distal section and a resonant section, the distal section being longer than the resonant section, the horn coupled to the needle; and
    a driver configured and arranged to impart a twisting, rotative movement to the tip at an elevated resonant frequency sufficient to eliminate chatter otherwise present at lower resonant frequencies;
    wherein the heat generation reduction structure includes a tubing that is situated between the infusion sleeve and the phacoemulsification needle, the tubing having a texture that is less tacky than that of the infusion sleeve and provides less friction resistance to rubbing action than the infusion sleeve.

11. The instrument of claim 10, wherein the tubing is made of a polyimide material.

12. The instrument of claim 10, further comprising a controller of the driver that directs the driver to alter an amount, duration or type of ultrasound power imparted to the tip of the phacoemulsification needle based on an analysis that tracks a history of the ultrasound power over time and its effect on changing temperature.

13. The instrument of claim 10, further comprising a controller of the driver that directs the driver to introduce pauses in the twisting, rotative movement.

14. The instrument of claim 10, further comprising a controller of the driver that directs the driver to vary an amplitude of the ultrasound power being applied.

15. The instrument of claim 10, wherein the driver is configured to impart the twisting, rotative movement to the tip at a resonant frequency of at least 40 kHz.

16. The instrument of claim 10, further comprising a controller of the driver that directs the driver to vary a duty cycle of the ultrasound power being applied.

17. The instrument of claim 10, further comprising a controller that tracks a history of ultrasound power over time.

18. The instrument of claim 10, further comprising a controller that tracks a temperature.

* * * * *